United States Patent
Maye et al.

(10) Patent No.: US 6,893,857 B1
(45) Date of Patent: May 17, 2005

(54) METHOD FOR USING HOPS ACID FOR CONTROLLING MICROORGANISMS IN A SUGAR-CONTAINING AQUEOUS PROCESS MEDIUM

(75) Inventors: John-Paul Maye, Washington, DC (US); David Beddie, Worcestershire (GB); Gunter Pollach, Gross-Enzersdorf (AT)

(73) Assignees: Beta Tec Hopfenprodukte GmbH, Nuremberg (DE); Zuckerforschung Tulln GmbH, Tulln (AT)

( * ) Notice: Subject to any disclaimer, the term of this patent is extended or adjusted under 35 U.S.C. 154(b) by 0 days.

(21) Appl. No.: 09/914,551

(22) PCT Filed: Feb. 22, 2000

(86) PCT No.: PCT/DE00/00485

§ 371 (c)(1),
(2), (4) Date: Nov. 20, 2001

(87) PCT Pub. No.: WO00/53814

PCT Pub. Date: Sep. 14, 2000

(30) Foreign Application Priority Data

Mar. 5, 1999 (DE) .......................... 199 09 827

(51) Int. Cl.$^7$ ............................ C12N 1/00; C12N 1/38; A23L 3/34
(52) U.S. Cl. ..................... 435/243; 426/61; 426/531; 426/532; 435/244; 435/256.8
(58) Field of Search ................... 426/61, 531–532; 435/243, 244

(56) References Cited

U.S. PATENT DOCUMENTS 5,286,506 A  2/1994  Millis et al. ................ 426/335

FOREIGN PATENT DOCUMENTS

EP          0681029      11/1995
WO          WO 97/33971  * of 1997

OTHER PUBLICATIONS

"Membrane Leakage In *Bacillus* Subtilis 168 Induced By The Hop Constituents Lupulone, Humulone, Isohumulone And Humulinic Acid", Teuber, et al. Abteilung Mikrobiologie, Institut Fur Botanik Der Technischen Universitat Munchen, *Arch. Mikrobiol.* 94, 159–171 (1973)–Springer–Verlag 1973.

* cited by examiner

Primary Examiner—David M. Naff
Assistant Examiner—Deborah K. Ware
(74) Attorney, Agent, or Firm—Merchant & Gould P.C.

(57) ABSTRACT

The invention relates to a method for controlling microorganisms in a sugar-containing aqueous process medium, especially in the sugar industry, using hop bitter acid as active substance. The hop bitter acid is dissolved in an aqueous alkaline medium and added to the process medium. The pH value of the added solution is higher than the pH value of the process medium and the hop bitter acid passes from the dissociated to the indissociated form in the process medium.

25 Claims, 1 Drawing Sheet

METHOD FOR USING HOPS ACID FOR CONTROLLING MICROORGANISMS IN A SUGAR-CONTAINING AQUEOUS PROCESS MEDIUM

CROSS-REFERENCE TO RELATED APPLICATIONS

This application claims priority under 35 U.S.C. § 371 from PCT/DE00/00485, filed Feb. 22, 2000, which claims the benefit of German Appl. No. 199 09 827 1, filed Mar. 5, 1999.

DESCRIPTION

This invention concerns a procedure for combating microorganisms in a sugary, aqueous process medium, especially the sugar industry using hops acid as the active substance. The invention further concerns a method for the production of a solution of hops acid for use in the aforementioned procedure, as well as use of the hops acid for combating microorganisms in a sugary, aqueous process medium, in particular of the sugar industry.

The bacteriostatic action of hops acid has been known for a long time. Hops acids were used for many years for the preservation of beer. The use of hops acid in brewing has, however, retreated into the background through bacteria-free fermentation and racking.

Known from EP 0 681 029 A2 is a procedure for inhibiting thermophilic microorganisms in the presence of sugary, aqueous mediums, where a hops base additive, preferably hops extract, is furnished in liquid or emulsified form to the sugary, aqueous mediums of the sugar industry (i.e. extracts of sugar-containing plants), and is worked in at temperatures between 50° C. and 80° C. takes place. The solution of the hops acid extract is done in water, however also with addition of alcohol. Supplying the dissolved or emulsified hops product can be done continuously or discontinuously (shock dosing).

Already known from U.S. Pat. No. 5,286,506 is how to use hops acid for combating bacteria, in particular listeria in processed food products. Its use follows hereby due to the fact that solid processed food products are immersed in a solution of β-acid or sprayed with it.

Known from Arch. Mikrobiol. 94 (1973, pp. 159–171 is that hops acids in the range of a minimal concentration act bacteriostatically, however at higher concentrations act toxically. In the case of use of so-called "β-acids" as a special type of the hops acids, which according to the aforementioned publication show the highest bacteriostatic action in comparison to α-acid as well as iso-α-acids, because of low solubility certain concentrations of β-acid can not be exceeded.

At the earliest, still while combating thermophilic microorganisms, according to EP 0 681 029 A2, achieved by the prevailing high temperatures of the process medium there is a high solubility of β-acids and, therewith, a better efficiency.

The object of this invention consists of increasing the efficiency of the generic process.

DETAILED DESCRIPTION OF THE INVENTION

Figure 1:
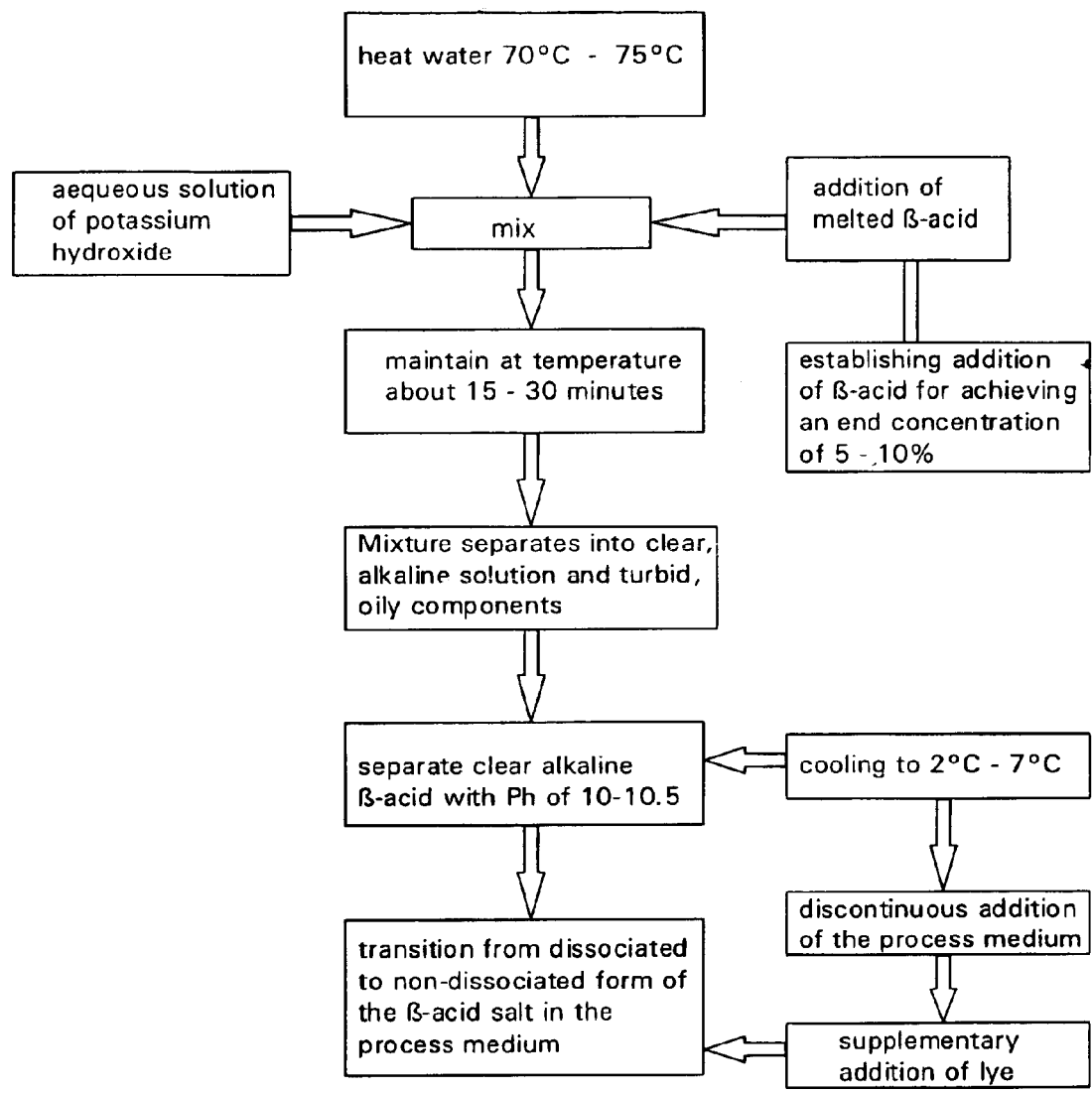
FIG. 1 is a schematic diagram illustrating a sequence of steps in accordance with a preferred process according to the invention.

The task is resolved in accord with the invention in that hops acid brought into solution in an aqueous alkaline medium is added to the process medium, whereby the pH value of the added-in solution is higher than the pH value of the process medium, and the hops acid in the process medium passes over from the dissociated form into the non-dissociated form. Because of the small dosage amount in added solution in comparison to the process medium, the solution after addition into the process medium assumes completely the pH value of the process medium, whereby the hops acid passes over from the dissociated form into the noon-dissociated, antibacterially active form. Astonishingly, it has been shown that the action of hops acid, when in the process medium it passes from the dissociated condition into the non-dissociated form, is particularly good. This has as a consequence that, for obtaining the desired action, the total insertion of hops acid can be greatly reduced in comparison to earlier times. On the other hand, also achievable is an increased action with the same dosage as earlier. The procedure according to the invention is used in the case of process mediums, in particular in the form of sugary plant extraction solutions of the sugar producing process.

Practically, the solution is added to the process medium periodically, i.e. an addition occurs at certain points in time within a short period of time, when local and short term high concentrations are adjusted (shock dosing). A dosing of this kind by means of the high local concentrations works against an adaptation of microorganisms.

Practically, the solution to be supplied to the process medium displays hops acid in a concentration of 2–40%, preferably 5–20%, particularly preferable 10–15%. High concentrations are particularly favorable from the point of view of temporary storage as well as with regard to transport.

The pH value of the solution added to the process medium lies in a range of 7.0–13.0, preferably 7.5–11.5, preferably 9.5–10.5. In this range, a particularly high efficiency is reached by use of this solution. The solution can be added without the danger of caustic action on the human skin. Moreover, in contrast to other chemical agents, the solution develops no unpleasant or health-endangering vapor pressure.

A particularly high efficiency results with the use of β-acids as hops acid. However, α-acids or a mixture of α-acids and β-acids can also find application. In the production of the solution, α-acids are converted into iso-α-acids, and as such retain their bacteriostatic action.

According to the invention, in the case of the hops acid—at least predominantly—we can be dealing with isomerized hops acids and/or with their derivatives, or a mixture thereof. Here, practically, we are dealing with tetrahydro-α-acid (THAA), or with hexahydro-β-acid (HHBA), and in the case of the isomerized hops acid derivatives with iso-α-acid (IAA), rho-iso-α-acid (RIAA), tetrahydro-iso-α-acid (THIAA) and/or hexahydroxide-α-acid or a mixture of the above compounds.

Practically, to be provided as an alkaline medium is an alkaline hydroxide, in particular potassium hydroxide and/or sodium hydroxide, or a mixture thereof. Practically, the concentration of the alkaline medium amounts to 0.1–5%, preferably 1–4%, preferably 2–3%.

A special variant of the procedure according to the invention is characterized by the fact that, besides addition of hops acid brought into solution, additionally supplied to the process medium is alkali liquor (lye), preferably in concentrations of 5–25%; undertaken thereby is a treatment under reinforced alkaline conditions. The reinforced alkaline conditions in the process medium take care of a delayed precipitation of the β-acids and, therewith, an additional increase in efficiency. This increase in efficiency works out particularly favorably in the case of discontinuous addition of the solution.

The solution, in particular in the case of the aforementioned range, can be supplied by manually pouring in, e.g. using the trough extraction system.

Alternatively, in the case of closed dosing systems, which are available in many sugar factories for emission-free dosing of formalin, the solution can be supplied over these dosing systems, i.e. combating of microorganisms can be undertaken while retaining the already existing procedural technology (closed dosing systems). The invention further concerns a procedure for producing a solution of hops acid for use in the procedure in accordance with claims 1–14, which comprise the following steps:

a) preparation of an aqueous medium;

b) heating;

c) addition of hops acid, in particular melted hops acid, with measurement of the amount of hops acid such that the end concentration lies within a prescribed concentration range;

d) addition of the alkaline medium for reaching a predetermined pH value;

e) mixing of the alkaline medium with the added hops acid;

f) maintaining the mixture in a high temperature range over a prescribed period of time;

g) separation of the hops acid solution from the mixture or vice-versa, as well as h) cooling the hops acid solution.

Through means of the above procedure, a solution can be prepared which, at high concentrations of hops acid, can be temporarily stored and/or transported. At the same time, the solution guarantees a reduction of the overall insertion amount of hops acid, in comparison to earlier procedures. The procedural steps can be changed in their sequence. The aforementioned sequence guarantees a very exact setting of the pH value of the solution.

Practical arrangements of the procedure according to the invention based on patent claim 13 are located in the other patent claims 14–18.

Further claimed in a collateral manner is the use of hops acid for combating microorganisms in a sugary, aqueous process medium of the sugar industry, which is characterized in such a way that hops acid brought into solution in an alkaline medium is added to the process medium, whereby the pH value of the solution is higher than the pH value of the process medium, and the hops acid in the process medium passes over from the dissociated to the non-dissociated form in accordance with procedural claims 1–12.

The single drawing FIGURE shows in a strongly simplified schematic sequence of the process the individual steps for execution of the procedure according to the invention.

For this purpose, one heats an aqueous solution to 70° C.–75° C. and brings into this solution melted β-acid-containing hops extract. The amount of hops extract is measured such that the end concentration of the acid in solution should lie at about 10–15%, whereby higher concentrations of β-acid are particularly favorable from the point of view of a temporary storage or a long transport. Potassium hydroxide is added until the predetermined pH value is reached.

The mixture is then maintained at temperature about 15–30 minutes.

The mixture separates into clear, alkaline β-acid solution along with turbid, oily components. The clear, alkaline β-acid solution with a pH value of preferably bout 10–10.5, is drawn off from the mixture and cooled to a temperature below room temperature, preferably 2–7° C. Next, it is supplied to the process medium in discontinuous fashion, i.e. shock dosing.

There, the solution mixes with the slightly acidic or at least less alkalinically-reacting process medium, whereby, because of the low dosing amount of highly concentrated β-acid solution, the mixture nearly completely assumes the pH value of the process stream, whereupon the β-acid passes over from its dissociated salt form into the non-dissociated, antibacterially active form.

The α-acids contained in the hops extract are converted during the production of the solution into iso-α-acids, and as such retain a bacteriostatic action.

A solution of this kind, because of a moderated alkalinity, displays favorable properties relative to transport, handling and temporary storage, and is stable over several months. Because of its composition, the solution can, for example, be dosed (measured) into trough extraction facilities of the sugar industry by manual pouring into hatches. There is neither a caustic action on human skin to be feared, nor does the alkaline solution, in comparison to other chemical agents, develop an unpleasant or health-endangering vapor pressure (as is the case with formalin). Likewise, because of the selected pH value of the solution, achievable with direct use of the solution is a strong increase in efficiency.

The solution can also be supplied through closed dosing systems that are available in many sugar factories for emission-free dosing of formalin, if the formalin pump is operated with soft water instead of formalin, and the alkaline hops acid solution is dosed into the suction line of the running pump. The alkaline solution can, hereby, be sucked in, pressed in by static height or by means of a second pump, whereby achieved by a short overrun of the water pump is a scavenging of the line.

When using the closed dosing system, the solution can be measured in, even under reinforced alkaline conditions by the additional use of alkali liquor (lye). In doing this, in parallel to the hops acid solution, measured into the process medium is lye in concentrations of 5–25%. Here in the case of temporary storage that would lead to β-acid losses, stronger alkaline conditions can also be selected for a short period of time. By supplementary use of lye and build up of alkaline striae in the process medium, achieved will be an at least slightly delayed precipitation or, to be precise, formation of the non-dissociated form of the β-acids and an additional improvement effect.

Finally, it is possible to start out right at the process medium, i.e. in the factory, from melted, commercially available hops extracts and, shortly before a shock dosing, to mix this with lye at elevated temperature. After a short solution time the entire mixture is measured in as a single shock dose. Also in doing this, short-time, stronger alkaline conditions can be selected, which in the case of a temporary storage would lead to losses in hops acid.

The process can be automated by time-control of the dosing pump and valves. Also, in this case the increase in efficiency that is the object of this invention also enters in.

Through means of the improved action, the total insertion of active substances is reduced, which is associated with various advantages. Either reduced costs result through reduced dosing or there is an increased action with the same dosing.

For hops products with the same concentration, transport volume is reduced by the increase in efficiency. Of further significance is that the solid residues of a sugar extraction are turned into feed, and in the case of extreme increase, the dose for combating partially adapted microorganisms of the products of oxidation of β-acids could lead to a bitter taste for feed. With an increase in efficiency, this disadvantage is reduced.

Dependent upon the environment and the legal situation, sugar factories have different optimal conditions for operation of the extraction system. In many cases, microorganisms in the lower concentration range are knowingly allowed in order to improve ability to express the extracted waste. In these types of factories, microorganism growth can be better limited by alkaline hops solutions. Other factories wish to suppress as completely as possible microorganism growth in the extraction system, in order to minimize sugar losses. Here also, an increase in the efficiency means a decreased insertion of active substances, and therewith a cost advantage.

The following examples take into account different arrangements in sugar factories.

EXAMPLE 1

A 40% solution of potassium hydroxide (30 kg) is added to a stirred solution of beta fraction (200 kg, containing 55% β-acids) along with water (900 liters) at 70° C. until a pH value of 10.5 is set. After a stirring period of two hours, the oil as well as the aqueous layers are allowed to separate. The aqueous layer is drawn off and cooled to 5°. Precipitates are removed in order to obtain an aqueous β-acid solution (1,000 liters) that is used is a sugar factory in an extraction tower, and with a processing capacity of 10,000 tons of beets per day. The existing formalin dosing facility is operated with soft water instead of formalin, and the alkaline solution is dosed into the suction line of the running formalin pump. For freely scavenging the line, post-rinsing for one minute is done with water. Dosing is done at three locations of the extraction stream, six times daily, with 17 liters of solution that corresponds in total to 31 g/ton of beets. With this dosage, the lactic acid content of the raw juice is limited to a value of 450 mg/kg, which is non-imparing to the pressibility of the waste.

EXAMPLE 2

Produced is a solution in accordance with Example 1, which, analogous to Example 1, however, is dosed with the additional use of sodium lye. During dosing of 14 liters of alkaline solution/dosing location, dosed at the same are 40 liters of 5% sodium lye, so that the alkaline conditions in the transport water stream, and during entrance into the juice stream, will be reinforced. Through means of the reinforced alkaline conditions, the desired effect is already reached at 25 g/tons of beets.

EXAMPLE 3

Produced is a solution in accordance with Example 1 and used in a sugar factory, with a DDS extraction system and a processing capacity of 10,000 tons of beets/day for combating microorganism activity, whereby no targeted fermentation should be allowed. The solution is dosed in by manually pouring into the pressurized water circuit and into the hatches 2 and 3 of the extraction system. Because of the manual handling, use of additional lye is rejected. Six times per day 11 liters are brought to the mentioned locations; this corresponds in total to 20 g/ton of beets. When a first return of microorganisms is recognized from the nitrite or lactic acid conditions, dosing is done once at an earlier point in time.

EXAMPLE 4

Available in a sugar factory with a processing capacity of 10,000 tons of beets/day, are contrivances for melting base extract and a vessel that can be temperature stabilized at 70° C. Lactic acid formation is to be limited in accordance with Example 1, whereby individual impacts are produced at various locations of the extraction system, time delayed at least 30 minutes. A half hour before an impact-dosing time, 20 liters of 70° C. warm water, 6 liters of 11% sodium lye and 3.5 liters of base extract are mixed and stirred up until the impact-dosing point in time. Next, the solution is measured in and the container therewith becomes free for preparation of the next batch.

What is claimed is:

1. Procedure for controlling a content of microorganisms in a sugary, aqueous process medium of extraction systems in a sugar industry using hops acid as an active substance, said procedure comprising the steps of:

bringing hops acid into solution in an aqueous alkaline medium to form a first solution, and adding said first solution to the process medium, whereby a pH value of the first solution is higher than a pH value of the process medium, and the hops acid in the process medium passes over from a dissociated form into a non-dissociated form.

2. Procedure according to claim 1, wherein
the addition of the first solution to the process medium is done in a discontinuous manner.

3. Procedure according to claim 1, wherein
the first solution contains hops acid at a concentration of 2–40%.

4. Procedure according to claim 1, wherein
said first solution has a pH value of 7.0–13.0.

5. Procedure according to claim 1, wherein
said hops acid is substantially a β-acid.

6. Procedure according to claim 1, wherein
said hops acid is an α-acid or an iso-α-acid.

7. Procedure according to claim 1, wherein
said hops acid comprises isomerized hops acid.

8. Procedure according to claim 1, wherein
said hops acid comprises tetrahydro α-acid (THAA), hexahydro-β-acid (HHBA), iso-α-acid (IAA), rho-iso-α-acid (RIAA), tetrahydro-iso-α-acid (THIAA), or hexahydroxide-iso-α-acid.

9. Procedure according to claim 1, wherein
said alkaline medium comprises an alkaline hydroxide.

10. Procedure according to claim 9, wherein
said alkaline medium contains a concentration of 0.1–5% alkaline hydroxide.

11. Procedure according to claim 1, wherein
an alkaline lye is also supplied to the process medium.

12. Procedure according to claim 1, wherein
the hops acid is dissolved in the alkaline medium as salt.

13. Procedure according to claim 1, wherein
the first solution is added to the process medium manually.

14. Procedure according to claim 1, wherein
the first solution is added to the process medium over already available dosing systems.

15. Procedure according to claim 1, wherein
said first solution contains hops acid at a concentration of 5–20%.

16. Procedure according to claim 1, wherein
said first solution contains hops acid at a concentration of 10–15%.

17. Procedure according to claim 1, wherein
said first solution has a pH value of 7.5–12.0.

18. Procedure according to claim 1, wherein
said first solution has a pH value of 9.5–11.0.

19. Procedure according to claim 1, wherein
said hops acid comprises an α-acid and an iso-α-acid.

20. Procedure according to claim 9, wherein
said alkaline hydroxide is selected from the group consisting of potassium hydroxide, sodium hydroxide, or both.

21. Procedure according to claim 19, wherein said alkaline medium contains a concentration of 0.1–5% alkaline hydroxide.

22. Procedure according to claim 19, wherein said alkaline medium contains a concentration of 1–5% alkaline hydroxide.

23. Procedure according to claim 19, wherein said alkaline medium contains a concentration of 2–4% alkaline hydroxide.

24. Procedure according to claim 9, wherein said alkaline medium contains a concentration of 1–5% alkaline hydroxide.

25. Procedure according to claim 9, wherein said alkaline medium contains a concentration of 2–4% alkaline hydroxide.

* * * * *